(12) United States Patent
Simmons, Jr.

(10) Patent No.: US 6,537,069 B1
(45) Date of Patent: Mar. 25, 2003

(54) METHOD AND APPARATUS FOR DENTAL IMPLANTS

(76) Inventor: Earl Wayne Simmons, Jr., #25, 2020 Babcock Rd., San Antonio, Bexar County, TX (US) 78229

( * ) Notice: Subject to any disclaimer, the term of this patent is extended or adjusted under 35 U.S.C. 154(b) by 0 days.

(21) Appl. No.: 09/968,228

(22) Filed: Oct. 1, 2001

(51) Int. Cl.⁷ .................................................. A61C 8/00
(52) U.S. Cl. ...................................................... 433/173
(58) Field of Search ................................. 433/172, 173, 433/174, 175, 176

(56) References Cited

U.S. PATENT DOCUMENTS

| | | | | |
|---|---|---|---|---|
| 3,919,772 A | * | 11/1975 | Lenczycki | 433/173 |
| 4,086,701 A | * | 5/1978 | Kawahara et al. | 433/174 |
| 5,302,127 A | * | 4/1994 | Crisio, Jr. | 433/173 |
| 5,564,925 A | * | 10/1996 | Shampanier | 433/173 |
| 5,622,500 A | | 4/1997 | Niznick | |
| 5,810,592 A | * | 9/1998 | Daftary | 433/172 |
| 5,890,902 A | * | 4/1999 | Sapian | 433/173 |
| 5,984,681 A | * | 11/1999 | Huang | 433/174 |
| 6,217,333 B1 | * | 4/2001 | Ercoli | 433/173 |
| 6,325,627 B1 | * | 12/2001 | Ashman | 433/173 |

OTHER PUBLICATIONS

Gerald A. Niznick, DMD, MSD; Controversies; Implant ConnectionsS+ Surfaces, A Technology Report for Discerning Dentists, Paragon Implant Company, Encino, CA.

* cited by examiner

Primary Examiner—Cary E. O'Connor
(74) Attorney, Agent, or Firm—Dennis Braswell

(57) ABSTRACT

A dental apparatus and method of dental reconstruction are provided in which a base (24) is set (112) into or on a jawbone, and one or more stabilizers (26) couple the base (24) to the jawbone. A dental fixture (86) is coupled (114) to the base (24). Also provided are one-piece dental implants (120 and 132).

33 Claims, 4 Drawing Sheets

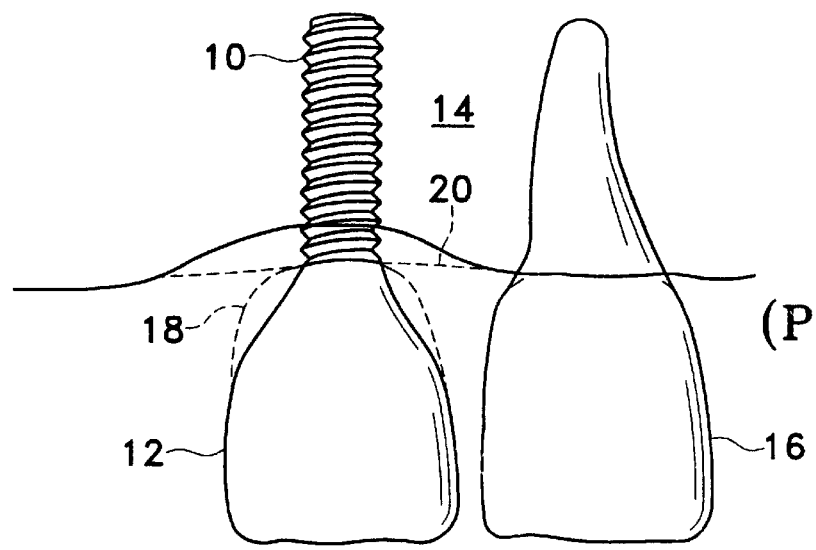
FIG. 1 (PRIOR ART)
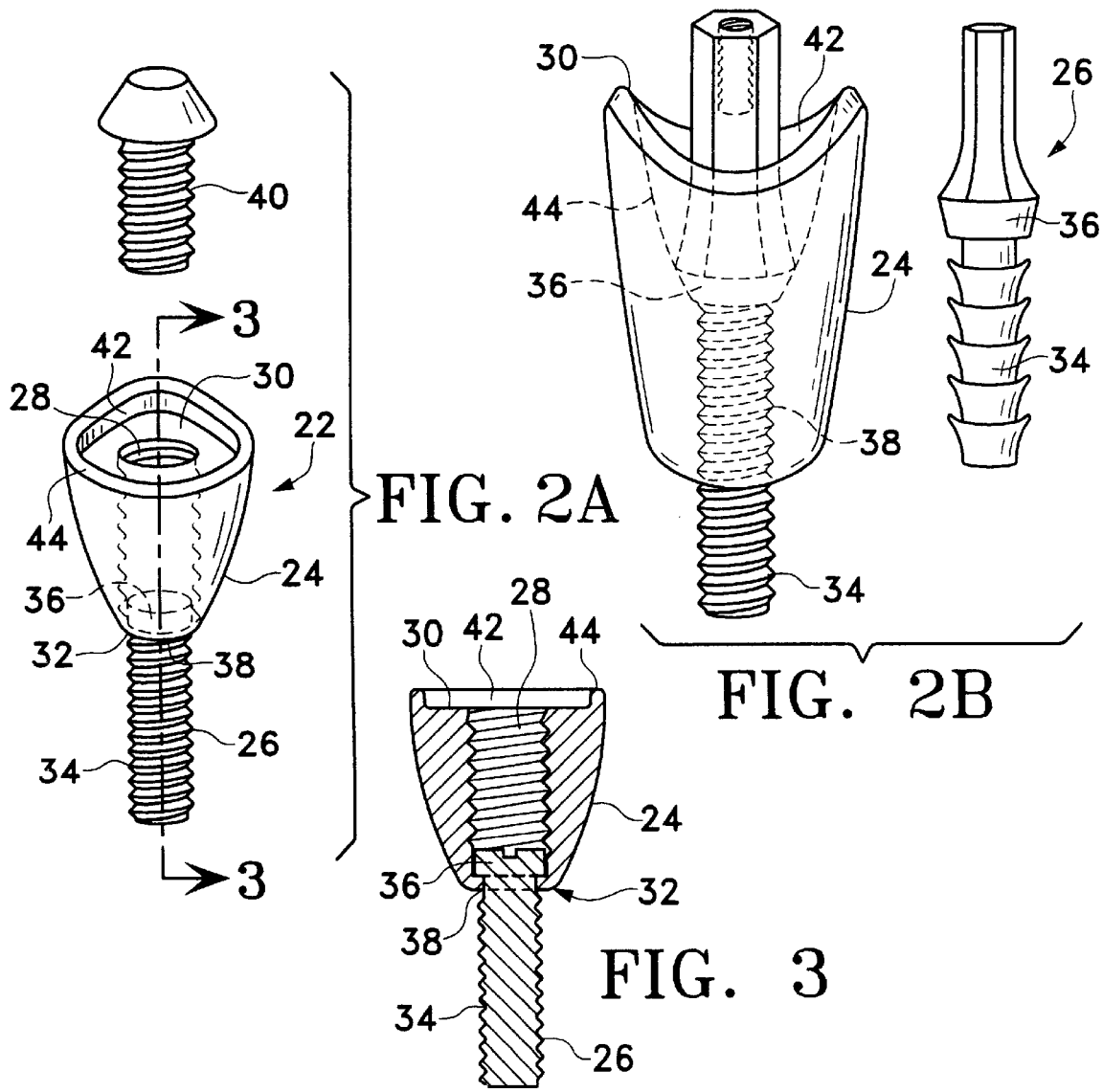
FIG. 2A
FIG. 2B
FIG. 3

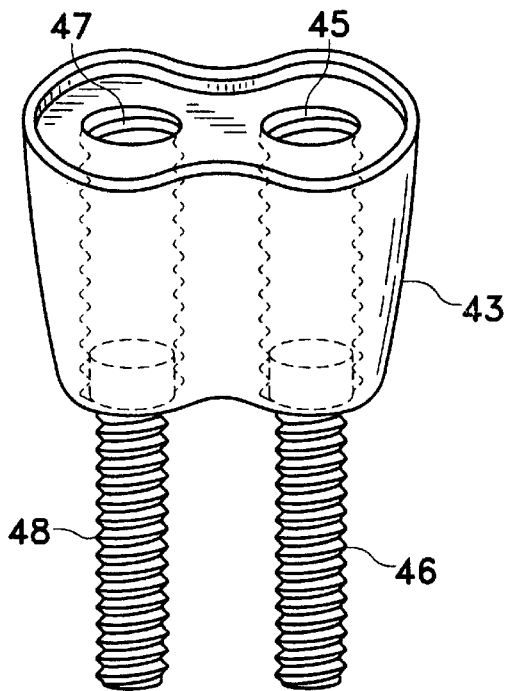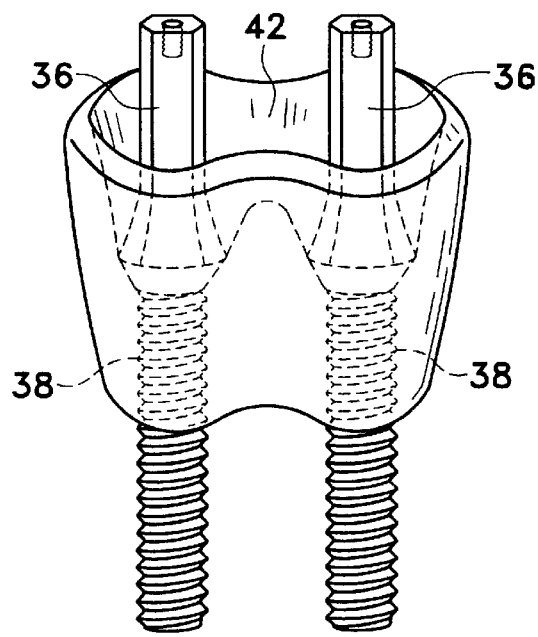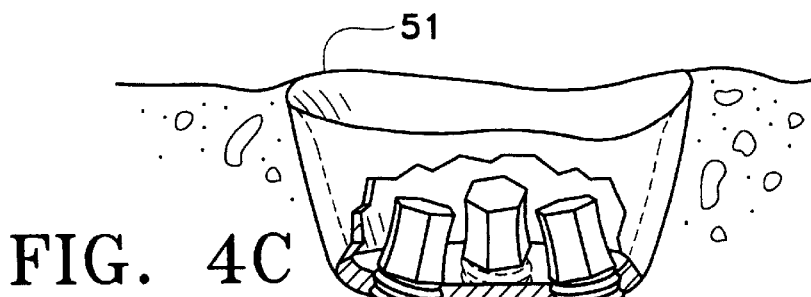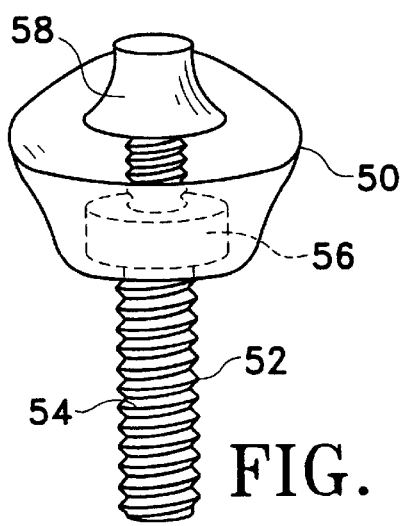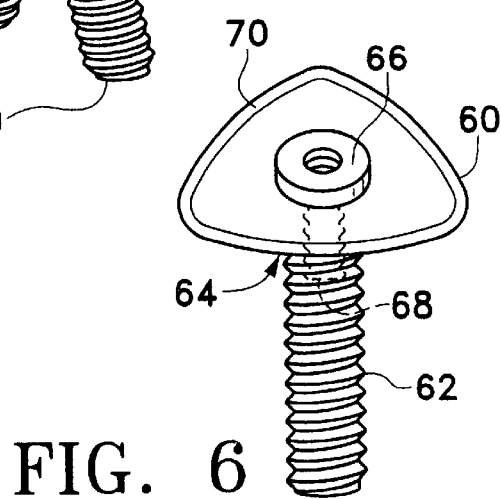

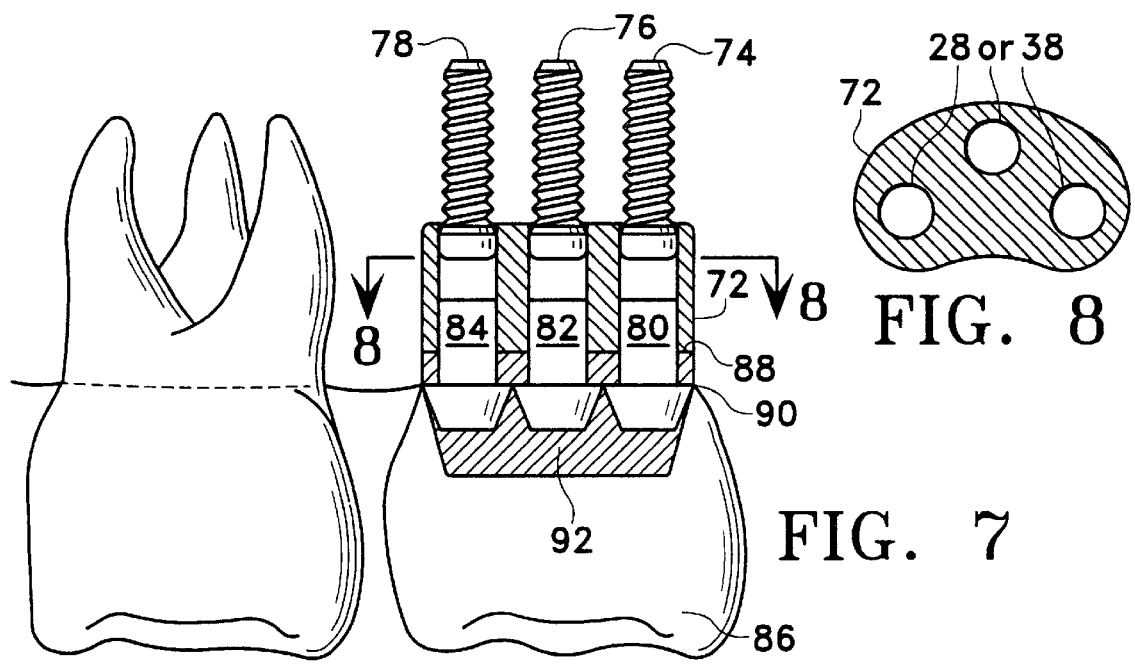
FIG. 7
FIG. 8
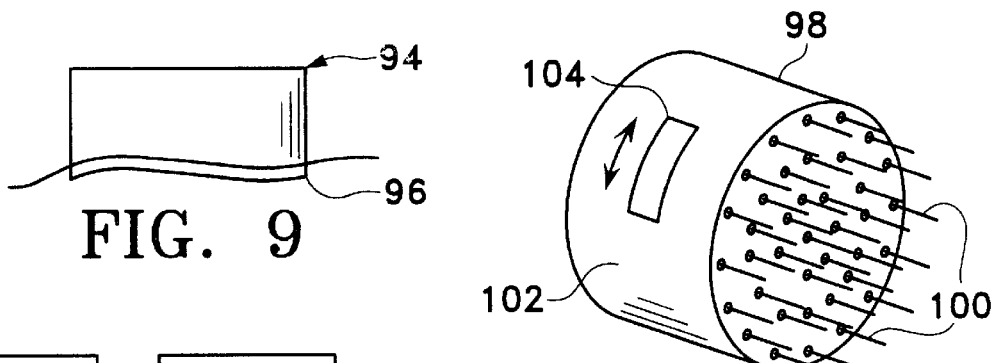
FIG. 9
FIG. 10
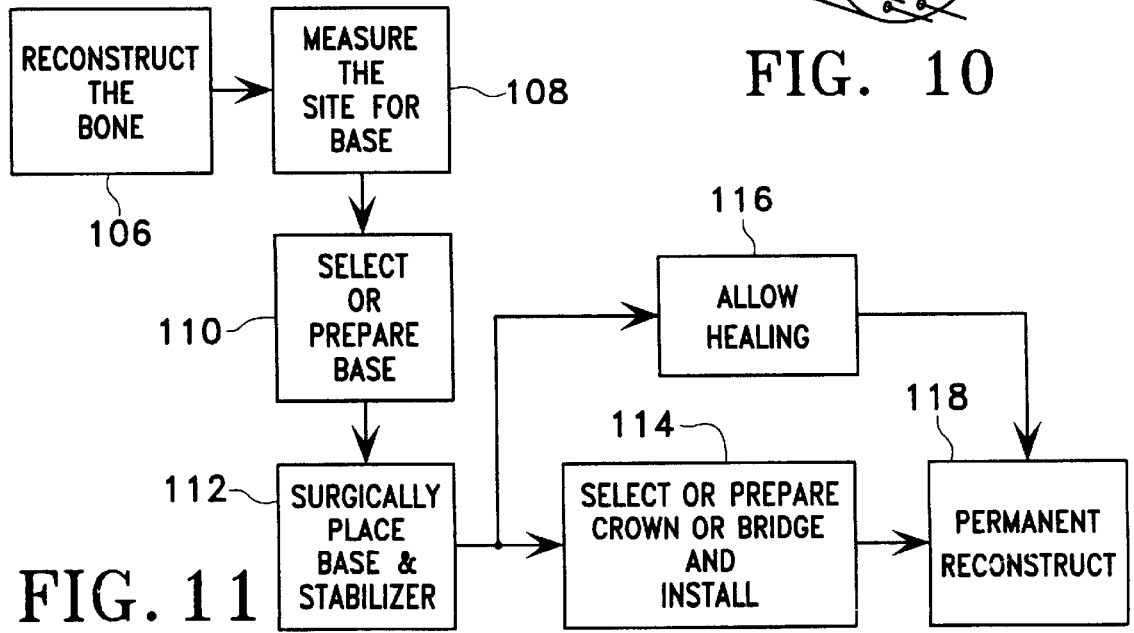
FIG. 11

METHOD AND APPARATUS FOR DENTAL IMPLANTS

TECHNICAL FIELD OF THE INVENTION

This invention relates generally to dentistry, and in particular to a method and apparatus for dental implants.

BACKGROUND OF THE INVENTION

For a variety of reasons, the loss of human teeth and related bony support structures is often a very difficult experience. In addition to the functional problems that result from such loss, significant emotional and psychological stresses are associated with the concerns about physical appearance and the ability to live, eat, and smile as normal, that arise after tooth loss.

In an effort to address these issues, many people turn to dental reconstruction to replace teeth. One class of replacements uses dental implants as tooth root replacements in the jawbone, with crowns, which resemble teeth and gums, attached to the implants. The present invention relates to that class of replacements.

The primary considerations in dental reconstruction are function, comfort, strength, aesthetics, and hygiene. Unfortunately, in many cases compromises must be made to one or more of these considerations to accommodate another. For example, to ensure that the reconstruction does not create hygienic problems, the crown must often be made with a non-anatomical emergence profile. Simply stated, the crown may not have the shape of a natural tooth. As another example, hygiene and aesthetics may be compromised to ensure adequate strength, such as when multiple implants are required.

To illustrate some of the problems with some prior art systems, shown in FIG. 1 is a prior art implant 10 and crown 12, with implant 10 implanted in jawbone 14. In the example of FIG. 1, the jawbone 14 has been resorbed, due to the loss of the natural root of the tooth, and is thus receded in the area of the implant 10, as compared to its normal extension shown in the area of natural tooth 16.

For hygienic reasons, it would be inappropriate to build crown 12 with the shoulders 18 shown in dashed lines, and thus crown 12 fails to provide an anatomical emergence profile. And, this problem persists even if the jawbone is not resorbed, or is reconstructed to its original architecture, shown by dashed line 20. FIG. 1 also highlights an aesthetic limitation of the illustrated prior art: in many cases it is possible to see the some of the implant between the crown and the gum line.

Therefore, a need has arisen for a dental implant and method of dental reconstruction that reduce or eliminate these problems.

SUMMARY OF THE INVENTION

In accordance with the teachings of the present invention, a dental device and method of dental reconstruction are provided which eliminate or substantially reduce the problems associated with prior art systems.

In particular, a dental apparatus is provided that comprises a base and one or more stabilizers coupling the base to a bone. A dental fixture may be coupled to the base. In particular embodiments, one or more of the following features are included: the base includes a rim defining a recessed area; the base is set into the bone; the rim is substantially flush with the bone; or the base has a plan profile that is substantially in the shape of a tooth being replaced.

In still other embodiments, one or more abutments are coupled to the base. Also, the base may include one or more bores into which the abutments are threaded. In other embodiments, one or more abutments are coupled to the one or more stabilizers or formed integrally therewith. Also, the base may have rounded shoulders, for example in a saddle shape, to support bone growth around and between implants.

Also provided is a method of dental reconstruction that includes setting a base into a jawbone, implanting one or more stabilizers through the base into the upper or lower jawbone, and attaching a dental fixture to the base. In other embodiments of this method, the jawbone is reconstructed, for example with bone grafting, before setting the base into the jawbone. Also, one or more abutments may be attached to the base or to the one or more stabilizers.

Also provided are one-piece dental implants. In one embodiment, a dental implant includes a bone end adapted for integration with a bone, and a crown end having shoulders for supporting bone growth. In a particular embodiment, the crown end has a saddle shape. Also, the bone end may be threaded.

Another one-piece dental implant embodiment includes a first section having an eccentric shape, the first section fitting into a tooth site. In a preferred embodiment of this one-piece implant, a second section has a concentric shape, the second section fitting into a hole at the bottom of the tooth site.

Important technical advantages are provided by the present invention. In particular, the base serves as a platform to which a crown can be fabricated and affixed, and can be shaped as desired, and, as an example, can be shaped to match the profile that a natural tooth would make at the area that it passes into the jawbone region. This shaping, along with setting of the base into the jawbone, allows for broader distribution of oblique forces (into the implant and surrounding bone) generated during mastication than in typical prior art systems, where forces are concentrated on a much smaller concentric diameter of the prior art implant.

Another important technical advantage is that the platform of the base allows for a more anatomical emergence profile than is often available with prior art reconstruction systems. This enhances the aesthetic appearance of the reconstruction, and avoids many hygienic problems.

Another important technical advantage is achieved with the shoulders that provide underlying support for bone (which may be grafted) and gum growth around and in the interproximal space between implants (or implants and teeth) to fill in unsightly gaps that can arise from existing systems.

BRIEF DESCRIPTION OF THE DRAWINGS

Reference is made in the description to the following briefly described drawings, which are not drawn to scale, with certain features enlarged for clarity, in which like reference numerals indicate like features:

FIG. 1 illustrates a prior art dental implant;

FIGS. 2A and 2B illustrate particular embodiments of mplants according to the teachings of the present invention;

FIG. 3 illustrates a side sectional view of the embodiment shown in FIG. 2A;

FIGS. 4A, 4B, and 4C illustrate other embodiments of implants according to the teachings of the present invention;

FIG. 5 illustrates another embodiment of an implant according to the teachings of the present invention;

FIG. 6 illustrates another embodiment of an implant according to the teachings of the present invention;

FIG. 7 illustrates another embodiment of an implant according to the teachings of the present invention;

FIG. 8 illustrates a plan view at section line B of FIG. 7;

FIG. 9 illustrates a side view of an embodiment of a shaped implant according to the teachings of the present invention;

FIG. 10 illustrates an embodiment of a tool for registering the outline of an implant base at a site of the implant, according to the teachings of the present invention;

FIG. 11 is a flow diagram of one embodiment of a method according to the teachings of the present invention;

DETAILED DESCRIPTION OF THE INVENTION

Figure 12:
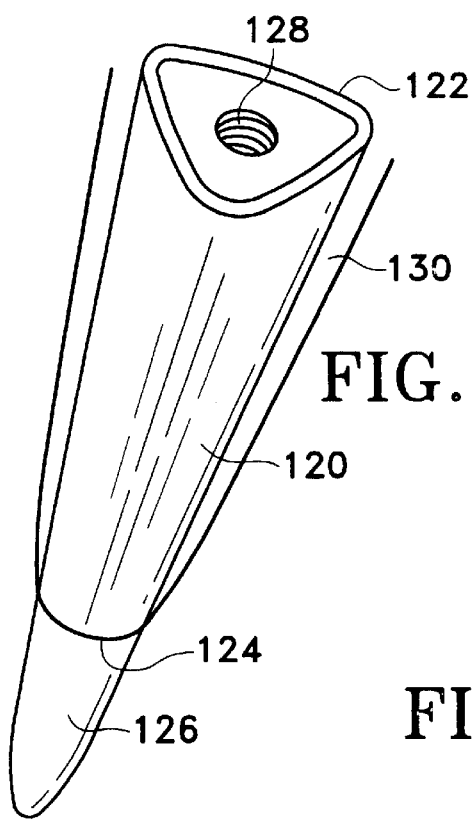
FIG. 12 illustrates a single-piece embodiment according to the teachings of the present invention.

The present invention allows for the use of eccentric shaped and non-eccentric shaped dental implant systems to provide many advantages over the prior art. In particular applications, the shape may be similar to a natural root form cross-section. Both single and multiple piece devices are described herein, with the single piece embodiments described in detail at FIGS. 12 and 13.

FIGS. 2A and 3 illustrate one embodiment of an implant system 22 according to the teachings of the present invention. The implant system 22 includes a base 24 and a stabilizer 26. Base 24 is set into the jawbone, and anchored with stabilizer 26. Base 24 and stabilizer 26 are preferably made of surgical grade Titanium, although any suitable material may be used.

In this particular embodiment, the base 24 includes a bore 28 passing from a crown side 30 toward a bone side 32 of the base 24. The stabilizer 26 includes a shaft 34 and a head 36. The shaft 34 passes through a hole (or passageway) 38 at the bone side 32 of the base 24, and is anchored into the jawbone, and thus should be adapted for osseointegration. The stabilizer head 36 has an outside diameter greater than that of the hole 38, and thus secures the base 24 to the jawbone. The outside diameter of stabilizer head 36 is also smaller than the inside diameter of the bore 28 and so passes through the bore 28. Although the start of hole (or passageway) 38 is shown close to the bone side 32, it could start closer to the crown side 30.

Bore 28 may be threaded to accommodate a threaded abutment 40. However, any suitable mechanism may be used to secure the abutment 40 to the base 24. For example, the stabilizer 26 may include a threaded bore within itself into which the abutment 40 is threaded. A crown, or other dental fixture, is cemented, glued, screwed, or otherwise affixed to the abutment 40 and base 24. These listed ways of affixing the crown are exemplary only. In another embodiment, a crown may be affixed directly to the base 24, and no abutment 40 is necessary. The crown can be colored as desired, depending on the site. For example, the portion of the crown nearest the base 24 may be colored gum color, and then tooth color beyond the gum line. Similarly, the base may be colored, for example with pink or tooth colors, as desired.

In a preferred rendition of this embodiment, base 24 includes a recess 42 defined by rim 44. This recess allows for excellent bonding or seating between the crown and the base 24. The recess is shown as relatively thin, but can be as deep as needed, or omitted altogether. The rim 44 (or crown end of the base) should be, although is not required to be, substantially flush with the jawbone. Thus, preferably the base is substantially set within the jawbone.

In some applications it may be appropriate to use a material, for example, but not by way of limitation, metal, plastic, ceramic, or glass-filled resin, to build an appropriate site for fixation of a crown or other dental fixture. The recess 42 provides an excellent space for building such a site, and the rim 44 provides a retainer for the material, and allows for a porcelain-metal interface, or a porcelain-porcelain interface, between the crown and base 24.

In typical applications, the base 24 is about 4 mm to 6 mm from the crown end 30 to the bone end 32. However, it can be much longer or shorter, depending on the needs of the application. Also, base hole (or passageway) 38 may be, but need not be, threaded to accommodate matched threads on the stabilizer 26. Stabilizer 26 may be threaded or include features to facilitate osseointegration (such as, without limitation, ribs, waists, or inverted ribs), and may be set in the bone in many ways, including, but not limited to, by screwing or tapping. However, it should be understood that the scope of the present invention, as described in connection with all embodiments herein, includes stabilizers with or without such features, and any device for securing the base to the bone is considered a stabilizer. Similarly, the outside of the base 24 may include features for facilitating osseointegration, such as, without limitation, ribs, waists, or inverted ribs.

FIG. 2B illustrates another embodiment of the present invention in which no bore 28 is used. The recess 42 forms a relatively large well that allows access to the hole (passageway) 38 (however, no such recess is needed). In the example shown, the stabilizer head 36 is an elongated hexagonally shaped member that accommodates a female drill, and hole (passageway) 38 may be threaded to accommodate a threaded stabilizer shaft 34. However, no such shape is needed. The head 36 can be shaped in any way, for example, without limitation, to accommodate drilling, to form an abutment for attachment of a crown, or to accommodate an abutment to be secured to the head. Also shown in FIG. 2B is an alternative stabilizer, by way of example only, in which the shaft 34 is barbed rather than threaded, and may be tapped into place.

In the embodiment shown in FIG. 2B, the crown side 30 of the base 24 includes rounded shoulders, which, in the particular embodiment shown, makes a saddle shape. When two or more implants are made side-by-side, or even when one implant is made alone, these shoulders provide underlying support for bone between and around the implants (or the implants and teeth), created, for example, with a bone graft. This support of interdental papillary or other bone is similar to that provided by natural tooth roots. This bone resides near the desired gum line, and gum tissue then heals over this bone, filling in the unsightly space that would otherwise exist between crowns or between teeth and crowns, when prior art implants are used. As discussed herein, the relatively wide base of the present invention alone often solves this unsightly space problem. The shoulders can further enhance that solution by facilitating gum tissue growth over supported bone. It should be understood that the saddle shape shown in FIG. 2B is exemplary only, and any structure that supports bone may be used. Furthermore, the saddle shape (or other such structure) does not have to be used, or may be used in connection with any of the embodiments described herein. Also, the use of structures to support bone growth may be used without a relatively wide base.

The use of base 24 solves many of the problems associated with the prior art. In general, the use of base 24 provides a broad platform from which a crown extends, thus allowing for several advantages. The base 24, and in particular the crown end 30, may be shaped in any way desired, to improve the strength of dental implants. In particular, the shape may—although need not—match the plan profile that a natural tooth would make at the area that it passes into the jawbone region. The broad profile allowed by the shape of the base, along with setting of the base into the jawbone, allows for more even distribution of oblique forces generated during mastication than in typical prior art systems (where forces are concentrated on the narrow implant). With the present invention, the forces are broadly distributed to the surrounding bone. For example, in a molar region, the natural tripod root support can be (although need not be) replicated, allowing for natural force distribution.

Also, the broad platform of base 24 allows for a more anatomical emergence profile than is often available with prior art reconstructions systems. This enhances the aesthetic appearance of the reconstruction, and avoids many hygienic problems.

FIG. 4A illustrates another embodiment of the present invention. This embodiment includes a base 43 shaped like a natural tooth that has two natural roots. This embodiment is similar to that of FIG. 2, but has a different shape, and the base 43 is anchored into the jawbone with two stabilizers 46 and 48 (which are seated at the bone end of bores 45 and 47). Thus, the emergence profile of a crown attached to this base 43, whether attached directly or to one or more abutments attached to the base 43, can be substantially anatomically correct, and the base 43 provides all the advantages discussed above.

FIG. 4B illustrates another two-stabilizer embodiment of the present invention similar to that of FIG. 4A, but wherein the bores 45 and 47 are not used. As described in connection with FIG. 2B, the recess 42 forms a relatively large well that allows access to the holes (passageway) 38. In the example shown, the stabilizer heads 36 are elongated hexagonally shaped members that accommodate a drill. However, no such shape is needed. The heads 36 can be shaped in any way to form abutments for attachment of a crown, or abutments can be secured to the heads. Also, the base of FIGS. 4A, 4B, and 4C (to be discussed), may be shaped to support bone, as discussed in connection with FIG. 2B.

FIG. 4C illustrates a particular three-stabilizer embodiment. As shown in FIG. 4C, stabilizers 49 may be angled into the bone to increase stability. The stabilizers 49 pass through base 51, for example through a threaded hole. In the particular example shown in FIG. 4C, which is exemplary only, the stabilizers 49 are 120 degrees apart (when projecting their separation angles onto a horizontal plane), and are tilted from a vertical axis. The particular placement depends on the needs of the application, and the particular topology of the available bone.

FIG. 5 illustrates an embodiment where a base 50 is anchored with a stabilizer 52 that includes a shaft 54, a flange 56, and integral abutment 58. In this embodiment, the base 50 may be relatively hollow, or include a larger bore, to accommodate the integral stabilizer/abutment 52. A crown or other dental fixture is fixed to the base 50 and the abutment 58, or, as discussed above, to the base alone if no abutment is needed (in which case abutment 58 would not be needed). Also, as discussed above, material, for example, but not by way of limitation, metal, plastic, or glass-filled resin, can be used to build an appropriate site on the base 50 or the abutment 58 for attachment of a crown or other dental fixture.

FIG. 6 illustrates another embodiment of the present invention, in which a relatively flat base 60 is used. Base 60 is again set into the jawbone, or on the jawbone, and anchored with stabilizer 62, which passes through a hole 64 in the base 60. A crown can be fixed to a head 66 of the stabilizer 62 or the base 60. The head 66 may be shaped as desired to form an integral abutment. Similarly, an abutment can be attached to the system, for example by threading it into a threaded bore 68 within stabilizer 62, or by any other approach. Indeed, such approaches may be used in connection with all the FIGUREs and embodiments described herein. U.S. Pat. No. 5,622,500, issued on Apr. 22, 1997, and entitled "Insertion Tool/healing collar/abutment," which is herein incorporated by reference in its entirety, provides examples of implants with internal threaded bores. Base 60 may include a rim 70 to form a recess, or it may be omitted.

FIGS. 7 and 8 illustrate another embodiment of the present invention in which a molar having three roots has been lost. The artificial replacement includes a base 72 anchored by three stabilizers 74, 76, and 78. It should be understood, however, that the number of stabilizers depends on the particular needs of the application, and that more or less stabilizers than natural roots can be used. Also, the stabilizers 74, 76, and 78 are shown as parallel. However, they may be angled, for example as shown in FIG. 4C. Also, the base 72 and stabilizers 74, 76, and 78 may be shaped other than as shown, for example, without limitation, like the embodiments of FIGS. 4B and 4C.

In FIG. 7, three abutments 80, 82, and 84 are illustrated. These abutments are shown extending beyond a recess 88 and rim 90. However, the abutments, if included at all, may be flush with or contained within the rim 90. Crown 86 is fixed to the abutments 80–84 and the base 72 with cement 92, which is shown surrounding the abutments and filling the recess. As discussed, other techniques could also be used for fixing the crown 86 to the base 72. Rim 90 may be rolled, chamfered, or otherwise shaped to provide an interface that minimizes tissue contact with any surface other than that of the base and the crown. FIG. 8 shows a plan view of section line B of FIG. 7. FIG. 8 shows that the embodiments can include, for example, a bore 28 and hole 38, or simply a hole 38 (which may be threaded to accommodate a threaded stabilizer shaft). Without the base of the present invention, for example, attempts to replace a molar's three roots would require a relatively large bony area (often unavailable), since close placement of conventional implants creates confined areas that present significant hygiene issues.

Because of the improved strength of the present invention, which results from the relatively broad base and the provision for multiple stabilizers at one site, fewer implants are needed for applications where bridges are appropriate. For example, an implant bridge can be anchored with the present invention at two ends of the bridge, with multiple implant bases, and fewer implants are needed on the whole, as there is much less need for implants all along the bridge.

FIG. 9 illustrates a side view of a base having a shaped rim 96 that follows the topographical contour of the bone at the reconstruction site. Such shaping is desirable, but not necessary. To measure such contours, a contour measuring tool 98, such as that illustrated in FIG. 10, can be used. Tool 98 includes a series of pin-like probes 100 that independently slide within body 102 in response to the topographical shape of the site being measured. Once the probes 100 are set against the site to be measured, a switch 104 is thrown to record the contour. The recording can be mechanical, by fixing the location of the probes and then manually transferring those: positions, or electrical. If electrical, sensors within the tool 98 measure the location of each probe 100, and record these locations for downloading for use in making the contoured base. Conversely, bases can be made, either in standard shapes and sizes or as custom pieces, and their topographical perimeter shape can be transferred to the bone site with a tool such as that shown in FIG. 9, so that a surgeon can cut the correct form for receiving the base.

As part of the present invention, a set of standard shaped devices may be prepared for the professional to choose from. For example, the set may have variously shaped bases for bicuspids, molars, canines, and incisors, and different sizes for each shape, along with variously sized stabilizers. From this set, the professional chooses the parts that are appropriate for the particular case. As an alternative, the professional may have the devices custom made, after analyzing the case. In this latter alternative, the professional may have the devices prepared with the aid of a CAD milling machine or powder metallurgy, among other known methods of forming parts. As examples of how to select the proper parts, the parts may be matched to the shape of an extracted tooth, if one is available, or to a gum impression.

As an illustration of an automated approach, data on the shape of a socket or other site (such as one prepared by bone graft), for example obtained from previous work on the site or from a laser or direct impression, is loaded into a CAD/CAM machine (computer). From this data, using a 3-D model, the computer designs an implant (base and/or stabilizers) to match the site. The dental professional can then review and approve the design, and have it manufactured by the machine. Generally the pieces should then be passivated and sterilized, and are then ready for surgical placement. This all may happen within a short period of time, so that the measuring and implanting can occur at one office visit by the patient.

FIG. 11 is a flow diagram of a method of dental reconstruction according to the teachings of the present invention. If there has been bone loss, or if the site is not appropriately sized for the desired implant, the bone is first reconstructed or built-up at the site, through known methods. This part of the method, if necessary, is shown at block 106, and may be done after blocks 108 and 110 (described below). The site or base is measured or otherwise reviewed at block 108 to match the topography of the site and the base. The measurement may be by, for example, without limitation, X-rays, MRI, CT scan, impressions, or other techniques. If a standard-sized (as discussed above) base and stabilizer system is used, then the base is selected at block 110. Or, if a custom base or stabilizer is to be used, the base is prepared at block 110 (which may be an automated approach as discussed above). At block 112, the base is surgically set to the jawbone, and then anchored to the jawbone with one or more stabilizers, after a surgeon has prepared the site for accepting the base, by cutting a hole to receive the base. Also, at block 112, an abutment may be attached.

At block 114, a provisional (or permanent, depending on the need for healing) crown or bridge is selected or prepared, and installed. Once the patient has healed (block 116), then a permanent crown or bridge selected or prepared, and then installed, at block 118, to the base or to one or more abutments attached to or formed integrally with the base or the one or more stabilizers.

In another embodiment of the present invention, shown in FIG. 12, a single-piece implant 120 is provided. In this embodiment, a crown side 122 of implant 120 is eccentrically shaped to provide the aesthetic and functional benefits desired. In particular, the eccentric (or occlusal) shape may match the natural root form of the tooth being replaced. In the example shown, the shape is a soft triangulated cross section that approximates the sectional anatomy of a particular tooth. However, the shape of any tooth may be approximated, and this embodiment is not limited to any particular tooth shape.

In a preferred embodiment, the eccentric shape continues (although it may taper or otherwise change shape, it is referred to herein as the eccentric shape) along the implant 120 toward a transition region 124. At region 124 the implant 120 changes to a concentric shaped section 126 which is set, for example by tapping, into the jawbone. Section 126 may include barbs or other features to facilitate osseointegration. Differently sized and shaped single-piece implants may also be included in the set described above.

The concentric section 126 (which may be tapered or not) allows a conventional concentric drill to be used to prepare the jawbone to accept the implant 120. However, concentric section 126 is not required as part of the present invention.

Implant 120 may include a bore 128 (which may be threaded) for receiving an abutment or other device for receiving a crown or other dental fixture. Also, an abutment or other device for receiving a crown or other dental fixture may be formed integrally with the implant 120, in which case no bore 128 is needed. Furthermore, the crown side 122 of implant 120 may include a recess to facilitate crown attachment.

In a particular application, the implant 120 may be set into an existing root socket (shown as socket 130). Concentric section 126, if included, is set further into the bone through the socket 130. Without a socket 130, or if the socket 130 is too small, a surgeon prepares an eccentric site for accepting the implant 120, and may also drill a concentric hole to accept the section 126 if necessary. The surgeon may use a osteotome to expand the osteotomy to fit the corresponding implant.

Figure 13B:
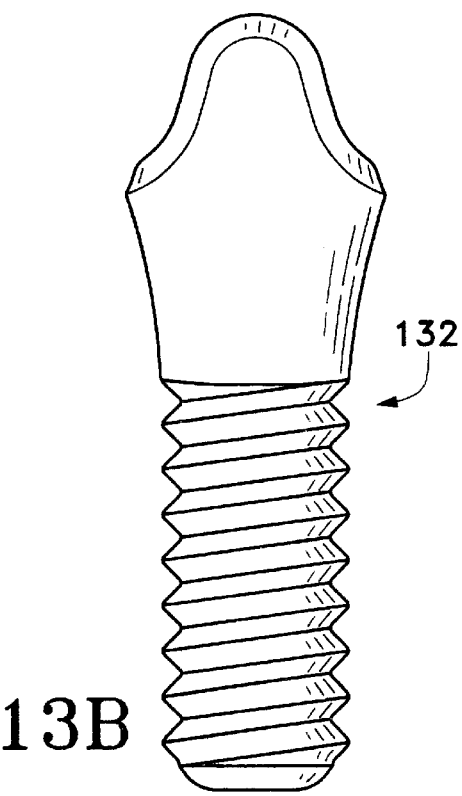
FIGS. 13A–13C illustrate three views of another single-piece embodiment according to the teachings of the present invention.
Figure 13A:
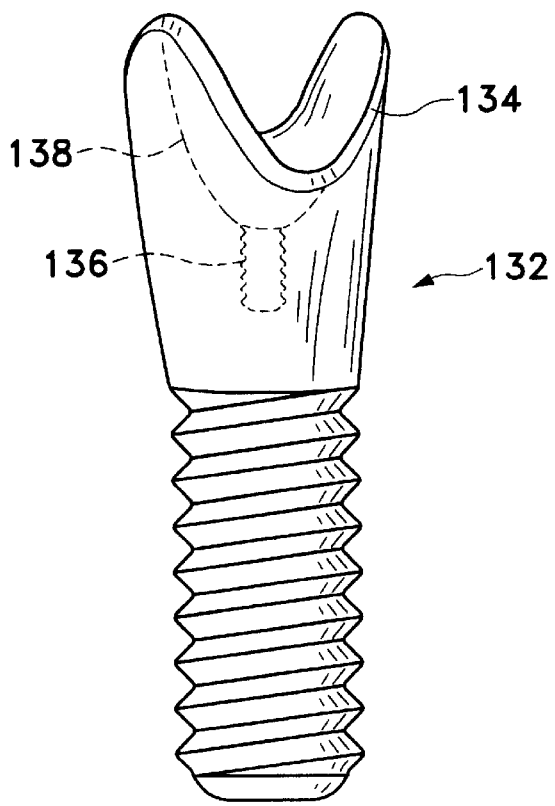
Figure 13C:
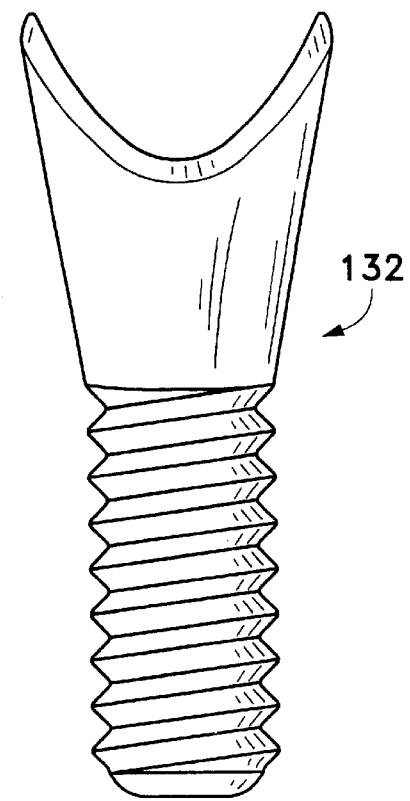

FIGS. 13A, 13B, and 13C illustrate three views of an embodiment of another one-piece implant 132. At its crown end, implant 132 includes rounded shoulders 134, which, in the particular embodiment shown, makes a saddle shape. When two or more implants are made side-by-side, or even when one implant is made alone, these shoulders can support bone between and around the implants or teeth, created, for example, with a bone graft. This bone resides near the desired gum line, and gum tissue then heals over this bone, filling in the unsightly space that would otherwise exist between crowns or between teeth and crowns, when prior art implants are used. It should be understood that the saddle shape shown in FIGS. 13A–13C is exemplary only, and any structure that supports bone may be used.

If desired, an abutment can be attached to the implant 132, for example at threaded bore 136. As shown in FIGS. 13A–13C, a recess 138 may be included to facilitate bone support and crown attachment.

The bone end of the implant 132 is shown with threads for screwing into the bone. However, any surface suitable for integration with the bone may be used, and the implant may be tapped in. Also, the structure for supporting bone (a saddle shape in the illustrated example) may be used in any of the other embodiments described herein, for example the multiple piece embodiments of FIGS. 2–8, and the single-piece embodiment of FIG. 12.

At the time of implant, the implants 120 and 132, and any of the bases or other stabilizers or implants described herein in connection with other embodiments, may be coated with platelet rich plasma ("PRP") and/or a PRP-bone matrix mix to facilitate fast generation of bone tissue for osseointegration. The PRP may be formed by taking a blood sample from the patient, and then centrifuging the blood to create the PRP.

Throughout the examples illustrated herein, the stabilizers and implants and the abutments may include internal female or external male hexagonal elements for driving in and out. However, other approaches can be used for driving the stabilizers, implants and abutments. Also, the devices may be tapped into place. Also, the base holes on the jawbone side of the bases may be tapered, or include a shaped well to accept a beveled or matched head on the stabilizer. Similarly, the crown end of the bore may be tapered or include a shaped well to accept a beveled or matched part on an abutment.

In this description, certain embodiments have been described with one, two, or three stabilizers for each base. However, it should be understood that these are illustrative examples, and other numbers of stabilizers and base shapes can be used with each embodiment. Similarly, features in each example can be interchanged with features in other examples. Also, certain materials, sizes, and approaches for fixing certain parts to others have been illustrated. Others can be used without departing from the intended scope of the present invention.

And, in general, although the present invention has been described in detail, it should be understood that various changes, alterations, substitutions, additions, and modifications could be made without departing from the intended scope of the invention, as defined in the following claims.

What is claimed is:

1. A dental apparatus, comprising:
    an eccentrically-shaped base, the base comprising a hole and a rim, the rim substantially following the eccentric shape of the base and defining a recessed area; and
    a stabilizer coupling the base to a bone through the hole.
2. The dental apparatus of claim 1, and further comprising a dental fixture coupled to the base.
3. The apparatus of claim 1, wherein the stabilizer comprises a shaft and a head, and the shaft passes through the hole.
4. The apparatus of claim 1, and further comprising an abutment coupled to the base.
5. The apparatus of claim 4, wherein the base comprises a bore, and the abutment is threaded into the bore.
6. The apparatus of claim 1, and further comprising an abutment coupled to the stabilizer.
7. The apparatus of claim 1, and further comprising an abutment integrally formed with the stabilizer.
8. The apparatus of claim 1, wherein the base is at least partially set into the bone.
9. The apparatus of claim 1, wherein the rim defines a non-planar surface.
10. The apparatus of claim 1, and further comprising one or more additional stabilizers coupling the base to the bone.
11. A dental apparatus, comprising:
    a base adapted to be at least partially set into a bone, wherein the base comprises
        a rim, the rim defining a surface that is non-planar,
        a hole, and
        a side, the side adapted to be in contact with the bone or bone graft material for stabilizing the dental apparatus; and
    a stabilizer passing through the hole and coupling the base to the bone.
12. The dental apparatus of claim 11, wherein the base comprises an eccentric shape, and the rim substantially follows the eccentric shape of the base.
13. The dental apparatus of claim 11, wherein the rim defines a recessed area.
14. The apparatus of claim 11, and further comprising one or more additional stabilizers coupling the base to the bone.
15. A dental apparatus, comprising:
    a base adapted to be at least partially set into a bone, wherein the base comprises a saddle shaped rim, a hole, and a side, the side adapted to be in contact with the bone or bone graft material for stabilizing the dental apparatus; and
    a stabilizer passing through the hole and coupling the base to the bone.
16. The dental apparatus of claim 15, wherein the base comprises an eccentric shape, and the rim substantially follows the eccentric shape of the base.
17. The dental apparatus of claim 15, wherein the rim defines a recessed area.
18. The apparatus of claim 15, and further comprising one or more additional stabilizers coupling the base to the bone.
19. A method of dental reconstruction, comprising:
    setting a base at least partially into a jawbone, wherein the base comprises a rim and a side, the rim defining a surface that is non-planar;
    implanting a stabilizer through the base into the jawbone;
    placing bone graft proximate the side of the base for stabilizing the base; and
    attaching a dental fixture to the base proximate the rim.
20. The method of claim 19, and further comprising attaching an abutment to the base.
21. The method of claim 19, and wherein attaching a dental fixture comprises cementing a crown to the base.
22. The method of claim 19, and further comprising attaching an abutment to the stabilizer.
23. The method of claim 18, the base comprising an eccentric shape and the rim substantially following the eccentric shape of the base to define a recessed area.
24. A dental implant, comprising:
    a first section having an eccentric shape and a first central axis, the first section fitting into a tooth site and comprising a side, adapted to be in contact with bone or bone graft material for stablizing the dental apparatus; and
    a second section comprising a substantially concentric shape and a second central axis, the second section fitting into a hole at the bottom of the tooth site, the first and second central axes being substantially coaxial.
25. The method of claim 24, wherein the first section comprises a rim that defines a non-planar surface.
26. A dental apparatus, comprising:
    an eccentrically-shaped base, the base comprising a rim that substantially follows the eccentric shape of the base and defines a recessed area, the base further comprising a side, the side adapted to be in contact with a bone or bone graft material for stabilizing the dental apparatus; and
    a stablizer coupling the base to the bone.
27. The apparatus of claim 26, and further comprising one or more additional stabilizers coupling the base to the bone.
28. A dental apparatus, comprising:
    a base, the base comprising a central axis and a hole, the hole being substantially coaxial with the central axis, the base further comprising a rim defining a recessed area surrounding the hole; and a stabilizer passing through the hole into a bone.

29. The apparatus of claim 28, wherein the base is adapted to be at least partially set into the bone and comprises a side adapted to be in contact with the bone or bone graft material for stabilizing the dental apparatus.

30. A dental implant, comprising:

a first section comprising an eccentric shape and a rim that substantially follows the eccentric shape, the rim defining a recessed area, and the first section fitting into a tooth site, the first section further comprising a side, the side adapted to be in contact with a bone or bone graft material for stabilizing the dental implant; and a second section comprising a substantially concentric shape, the second section fitting into a hole at the bottom of the tooth site.

31. The apparatus of claim 28, wherein the rim defines a non-planar surface.

32. A dental implant, comprising:

a first section comprising an eccentric shape and a rim, the rim defining a surface that is non-planar, the first section further comprising a side, the side adapted to be in contact with a bone or bone graft material for stabilizing the dental implant; and a second section comprising a substantially concentric shape, the second section fitting into a hole at the bottom of a tooth site.

33. The apparatus of claim 28, and further comprising one or more additional stablizers coupling the base to the bone.

* * * * *